United States Patent
Kinsho et al.

(10) Patent No.: US 6,472,543 B2
(45) Date of Patent: Oct. 29, 2002

(54) LACTONE COMPOUNDS HAVING ALICYCLIC STRUCTURE AND THEIR MANUFACTURING METHOD

(75) Inventors: Takeshi Kinsho; Takeru Watanabe; Koji Hasegawa; Tsunehiro Nishi; Mutsuo Nakashima; Seiichiro Tachibana; Jun Hatakeyama, all of Nakakubiki-gun (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 09/897,985

(22) Filed: Jul. 5, 2001

(65) Prior Publication Data

US 2002/0016477 A1 Feb. 7, 2002

(30) Foreign Application Priority Data

Jul. 6, 2000 (JP) .................................... 2000-205217

(51) Int. Cl.$^7$ .............................................. C07D 407/00
(52) U.S. Cl. ....................................... 549/295; 549/326
(58) Field of Search .................................. 549/295, 326

(56) References Cited

FOREIGN PATENT DOCUMENTS

EP          1149825 A2  *  10/2001

OTHER PUBLICATIONS

Hasegawa, Koji et al, 'Ester compounds, polymers, resist compositions and patterning process' CA 135:336914 (2001).*

* cited by examiner

*Primary Examiner*—Amelia Owens
(74) *Attorney, Agent, or Firm*—Millen, White, Zelano & Branigan, P.C.

(57) ABSTRACT

Lactone compounds of formula (1) are novel and useful as monomers to form base resins for use in chemically amplified resist compositions adapted for micropatterning lithography.

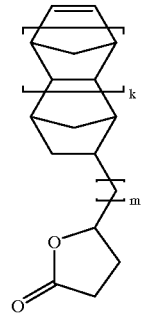

(1)

Letter k is 0 or 1 and m is an integer of 1–8.

4 Claims, No Drawings

LACTONE COMPOUNDS HAVING ALICYCLIC STRUCTURE AND THEIR MANUFACTURING METHOD

This invention relates to novel lactone compounds useful as monomers to form base resins for use in chemically amplified resist compositions adapted for micropatterning lithography, and methods for preparing the same.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

The resist materials for use in photolithography using light of an excimer laser, especially ArF excimer laser having a wavelength of 193 nm, are, of course, required to have a high transmittance to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low freedom of polymerization. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel lactone compound useful as a monomer to form a polymer for use in the formulation of a photoresist composition which exhibits firm adhesion and high transparency when processed by photolithography using light with a wavelength of less than 300 nm, especially ArF excimer laser light as the light source. Another object is to provide a method for preparing the lactone compound.

We have found that a lactone compound of formula (1) can be prepared in high yields by a simple method to be described later, that a polymer obtained from this lactone compound has high transparency at the exposure wavelength of an excimer laser, and that a resist composition comprising the polymer as a base resin is improved in adhesion to substrates.

In one aspect, the invention provides a lactone compound of the following general formula (1).

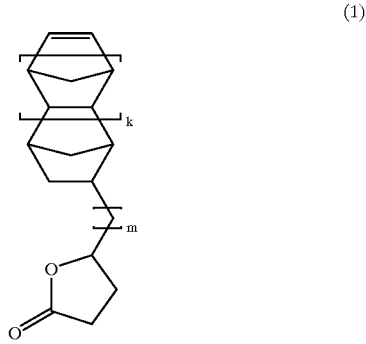

(1)

Herein, k is 0 or 1 and m is an integer of 1 to 8.

In another aspect, the invention provides methods for preparing the lactone compound of formula (1).

A first method for preparing a lactone compound of formula (1) according to the invention involves the steps of reacting an oxirane compound of the following general formula (2) with a metallomalonate to form a hydroxy diester compound of the following general formula (3), followed by hydrolysis, decarboxylation and lactonization.

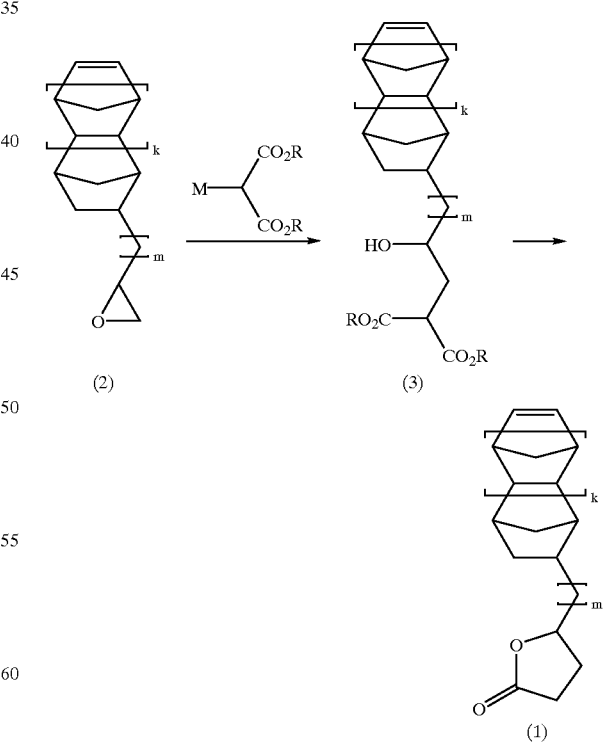

Herein, k and m are as defined above, R is alkyl such as methyl, ethyl or t-butyl, M is Li, Na, K, MgY or ZnY, and Y is halogen.

A second method for preparing a lactone compound of formula (1) according to the invention involves the steps of reacting an organometallic compound of the following general formula (4) with a 3-alkoxycarbonylpropionyl chloride to form a keto ester compound of the following general formula (5), followed by reduction and lactonization.

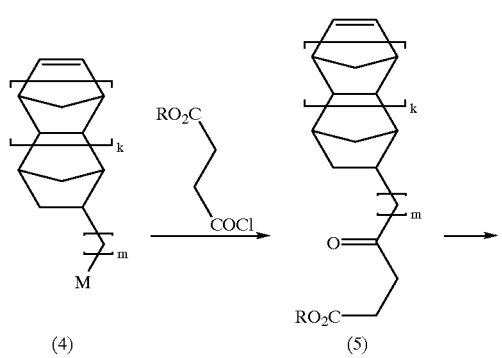

Herein, k, m, R and M are as defined above.

A third method for preparing a lactone compound of formula (1) according to the invention involves the steps of reacting an aldehyde compound of the following general formula (6) with lithium 3-lithiopropionate to form a hydroxycarboxylic acid compound of the following general formula (7), followed by lactonization.

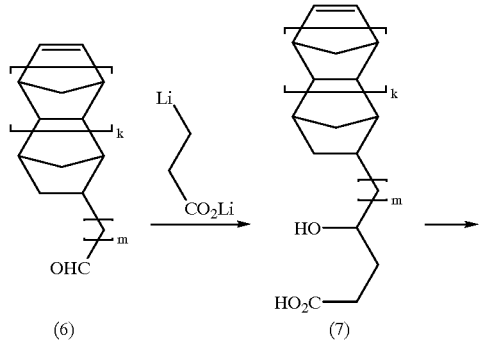

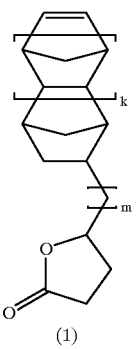

Herein, k and m are as defined above.

DESCRIPTION OF THE PREFERRED EMBODIMENT

The lactone compounds of the invention are of the following general formula (1).

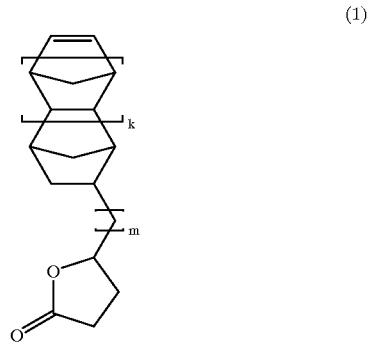

Herein k is 0 or 1 and m is an integer of 1 to 8 (i.e., $1 \leq m \leq 8$).

Illustrative examples of the lactone compound are given below.

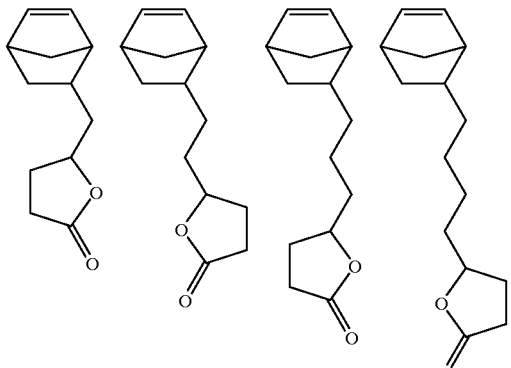

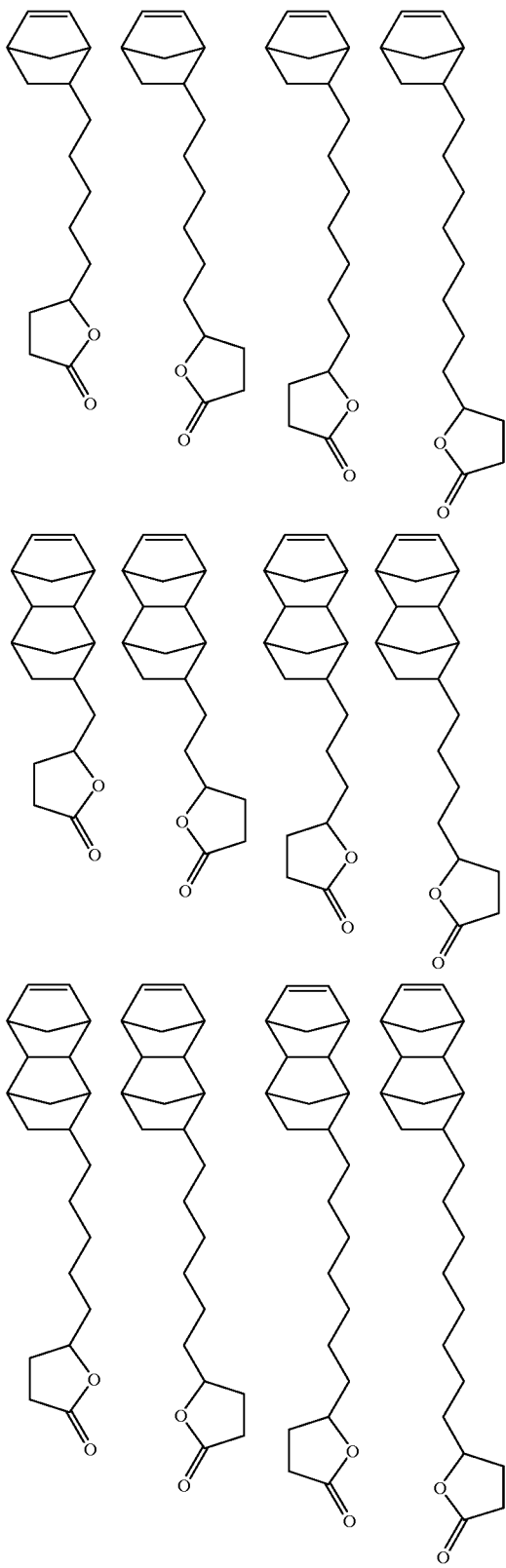

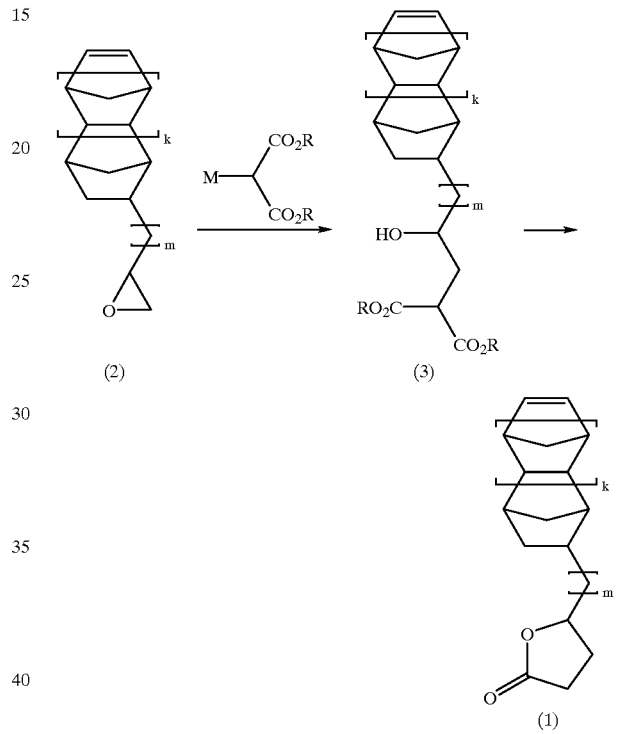

separated apart from the polymer backbone by an alkylene group. By selecting a lactone compound having an optimum alkylene chain as the monomer to form a polymer, the polymer as a whole can be adjusted to an appropriate compatibility and controlled in dissolution properties.

The lactone compounds of the invention can be produced by the following three methods, for example, but the invention is not limited to these methods.

The first method involves the steps of reacting an oxirane compound (2) with a metallomalonate to form a hydroxy diester compound (3), followed by hydrolysis, decarboxylation and lactonization, thereby producing the desired lactone compound (1).

Herein k and m are as defined above, R is an alkyl group such as methyl, ethyl or t-butyl, M is Li, Na, K, MgY or ZnY, and Y is a halogen atom.

The first step is to add a metallomalonate, prepared by a conventional method, to an oxirane compound (2) to form a hydroxy diester compound (3).

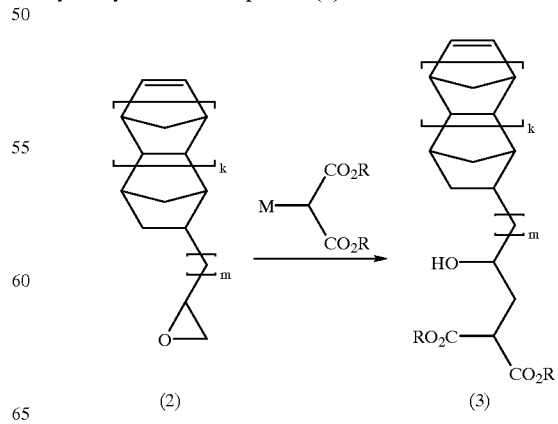

It is believed that resist polymers obtained using these lactone compounds as the monomer exhibit good adhesion to substrates because the butyrolactone moiety regarded as a polar group that brings out adhesion is positioned at a site Ring opening of the oxirane ring occurs preferentially from the desired methylene terminal side over the sterically hindered methine side. The amount of metallomalonate used is preferably 0.9 to 3 mol, more preferably 1.0 to 1.8 mol per mol of the oxirane compound. Depending on reaction conditions, a solvent may be selected from ethers such as tetrahydrofuran, diethyl ether, di-n-butyl ether and 1,4-dioxane, hydrocarbons such as n-hexane, n-heptane, benzene, toluene, xylene and cumene, alcohols such as methanol, ethanol, isopropyl alcohol and tert-butyl alcohol, and polar aprotic solvents such as dimethyl sulfoxide and N,N-dimethylformamide, alone or in admixture of any. The reaction temperature and time vary over a wide range. In one example wherein sodium anions which are prepared from malonate and sodium alkoxide in dry alcohol are used as a reagent, the reaction temperature preferred for rapidly driving the reaction to completion is from room temperature to the reflux temperature, and especially from 50° C. to the reflux temperature. The reaction time is desirably determined by monitoring the reaction until the completion by gas chromatography (GC) or silica gel thin-layer chromatography (TLC) because higher yields are expectable. The reaction time is usually about 1 to about 20 hours. From the reaction mixture, the hydroxy diester compound (3) is obtained by a conventional aqueous work-up procedure. If necessary, the compound (3) may be purified by any conventional technique such as distillation, chromatography or recrystallization. Often the crude product has a sufficient purity as a substrate for the subsequent step and can be thus used in the subsequent step without purification.

The second step involves hydrolysis, decarboxylation and lactonization (dehydrative condensation) to yield the desired lactone compound (1).

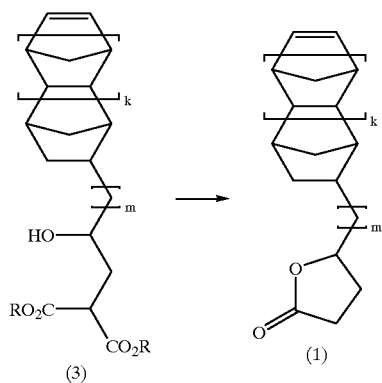

In an example wherein the alkyl group of the malonate used is a primary alkyl group such as methyl or ethyl (that is, R=CH$_3$ or C$_2$H$_5$), the ester is hydrolyzed or saponified using an aqueous alkaline solution, and then neutralized to form a hydroxy dicarboxylic acid. The resulting hydroxy dicarboxylic acid is converted to the lactone compound by heating in the presence of an acid catalyst to effect simultaneous decarboxylation and cyclization.

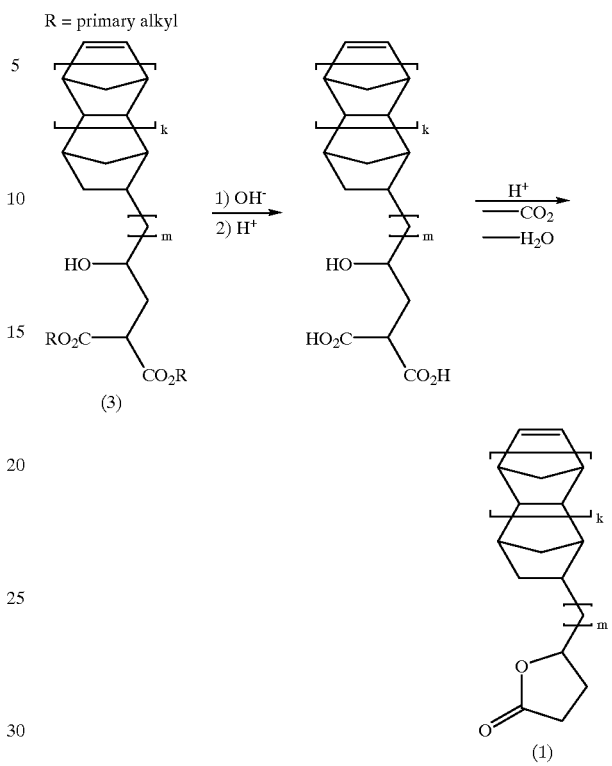

Herein, k and m are as defined above, and R is a primary alkyl group such as methyl or ethyl.

For the alkaline hydrolysis, use of aqueous solutions of hydroxides such as sodium hydroxide, potassium hydroxide, lithium hydroxide and barium hydroxide is preferred. The aqueous alkaline solution is preferably used in an amount of 2 to 10 mol, especially 2 to 4 mol per mol of the hydroxy diester compound (3). Alkaline hydrolysis can be effected in a solventless system although use may be made of organic solvents including ethers such as tetrahydrofuran, diethyl ether, di-n-butyl ether and 1,4-dioxane, alcohols such as methanol, ethanol, isopropyl alcohol and tert-butyl alcohol, and hydrocarbons such as n-hexane, n-heptane, benzene, toluene, xylene and cumene. The reaction temperature for alkaline hydrolysis is generally in the range of 0 to 100° C., and heating at a temperature of 50 to 100° C. is preferred to achieve rapid progress of reaction. Examples of the acid used for neutralization and decarboxylation/lactonization include inorganic acids such as hydrochloric acid, hydrobromic acid, sulfuric acid and nitric acid and organic acids such as oxalic acid, p-toluenesulfonic acid, and benzenesulfonic acid. As the acid catalyst for promoting decarboxylation/lactonization, the excess of acid left at the end of neutralization may be utilized or an acid of the same or different type may be newly added. In either case, the acid is used in an amount of 0.01 to 10 mol, especially 0.1 to 0.5 mol per mol of the hydroxy dicarboxylic acid. The reaction can be accelerated by positively removing the water formed upon lactone cyclization from the reaction system, for example, by azeotropical removal of water using a hydrocarbon such as n-hexane, n-heptane, benzene, toluene, xylene or cumene. Alternatively, the reaction may be carried out in vacuum in order to accelerate decarboxylation.

In another example wherein the alkyl group of the malonate used is a tertiary alkyl group such as tert-butyl (that is, R=t-C$_4$H$_9$), elimination of the tertiary alkyl group, decarboxylation and lactonization (dehydrative condensation) can be carried out simultaneously under acidic conditions, not by way of alkaline hydrolysis.

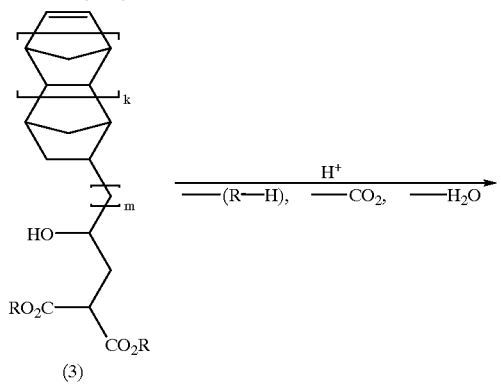

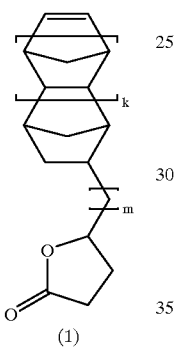

Herein, k and m are as defined above, and R is a tertiary alkyl group such as t-butyl. (R—H) is an alkene corresponding to the alkyl group R from which a hydrogen atom is eliminated. For example, (R—H) is isobutene when R is t-butyl.

Herein, an acid selected from inorganic acids such as hydrochloric acid, hydrobromic acid, sulfuric acid and nitric acid and organic acids such as oxalic acid, p-toluenesulfonic acid, and benzenesulfonic acid is used in an amount of 0.01 to 10 mol, preferably 0.1 to 0.5 mol per mol of the hydroxy diester compound. The reaction can be accelerated by positively removing the water formed upon lactone cyclization from the reaction system, for example, by azeotropical removal of water using a hydrocarbon such as n-hexane, n-heptane, benzene, toluene, xylene or cumene. Alternatively, the reaction may be carried out in vacuum in order to accelerate decarboxylation.

From the reaction mixture, the target lactone compound (1) is obtained by a conventional aqueous work-up step. If necessary, the compound (1) can be purified by any conventional technique such as distillation, chromatography or recrystallization.

In the second method, the desired lactone compound (1) is prepared by reacting an organometallic compound (4) with a 3-alkoxycarbonylpropionyl chloride to form a keto ester compound (5), followed by reduction and lactonization (dehydrative condensation).

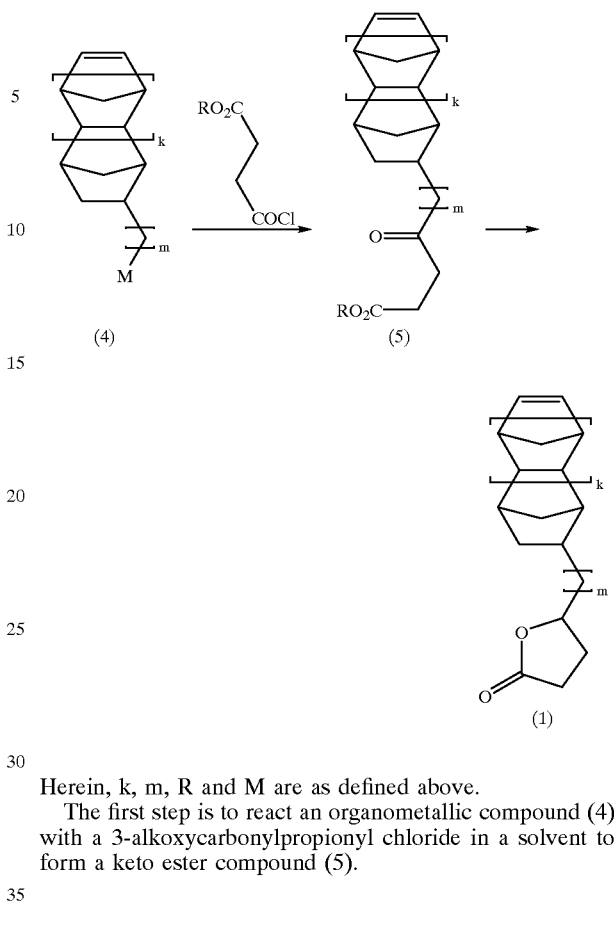

Herein, k, m, R and M are as defined above.

The first step is to react an organometallic compound (4) with a 3-alkoxycarbonylpropionyl chloride in a solvent to form a keto ester compound (5).

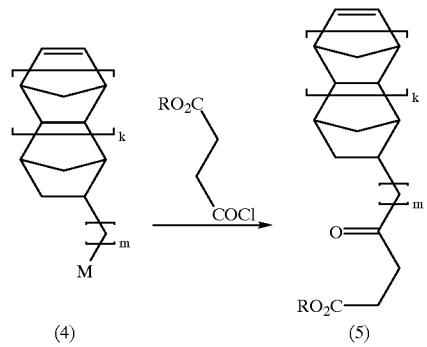

It is important at this stage that reaction takes place preferentially at the acid chloride site rather than at the ester site of the 3-alkoxycarbonylpropionyl chloride. This is accomplished by properly selecting the type of organometallic reagent, catalyst and reaction conditions.

The organometallic compound is prepared by a conventional method from a corresponding halogen compound or by transmetallation from an organometallic reagent of different metal. The solvent may be selected in accordance with reaction conditions from ethers such as tetrahydrofuran, diethyl ether, di-n-butyl ether and 1,4-dioxane, hydrocarbons such as n-hexane, n-heptane, benzene, toluene, xylene and cumene, and polar aprotic solvents such as dimethyl sulfoxide and N,N-dimethylformamide, alone or in admixture of any. There may be used as an auxiliary a compound having a ligand such as N,N,N',N'-tetramethylethylenediamine (TMEDA), hexamethylphosphoric triamide (HMPA), N,N'-dimethylpropyleneurea (DMPU) or 1,3-dimethyl-2-imidazolidinone (DMI). The catalyst which can be used is selected from compounds of transition metals such as iron, copper, palladium, nickel, cadmium and vanadium. An appropriate amount of the 3-alkoxycarbonylpropionyl chloride used is 1.0 to 5 mol, preferably 1.3 to 2 mol per mol of the organometallic reagent.

Reaction conditions vary over a wide range depending on the combination of reagent, solvent and catalyst. In one example using tetrahydrofuran as the solvent and a Grignard reagent (corresponding to M=MgY) as the organometallic compound, in the absence of the transition metal catalyst, reaction is effected at a low temperature, specifically −78° C. to room temperature, and especially −70° C. to 0° C. In this example, dropwise addition of the Grignard reagent to the 3-alkoxycarbonylpropionyl chloride solution, known as reverse addition, is effective. In another example using tetrahydrofuran as the solvent, a Grignard reagent (corresponding to M=MgY) as the organometallic compound, and an iron salt (e.g., Fe(acac)$_3$) as the transition metal catalyst in a catalytic amount (e.g., 0.01 to 0.5 mol per mol of the Grignard reagent), reaction is effected at a temperature of −10° C. to 50° C., and especially 0° C. to 30° C. In a further example using tetrahydrofuran or N,N-dimethylformamide as the solvent, an organozinc reagent (corresponding to M=ZnY) as the organometallic compound, and a palladium compound (e.g., Pd(PPh$_3$)$_4$) or nickel compound (e.g., NiCl$_2$(dppp)) as the transition metal catalyst in a catalytic amount (e.g., 0.01 to 0.5 mol per mol of the organozinc reagent), reaction is effected at a temperature of 0° C. to 80° C., and especially room temperature to 50° C. In a still further example using a Grignard reagent (corresponding to M=MgY) or organic lithium reagent (corresponding to M=Li) as the organometallic compound, and a cuprous salt (e.g., CuCl or CuBr) as the transition metal catalyst in a stoichiometric amount (e.g., 1.0 to 2.0 mol per mol of the organometallic reagent), reaction is effected at a temperature of 0° C. to 80° C., and especially room temperature to 50° C. The reaction time is desirably determined by monitoring the reaction until the completion by GC or silica gel TLC because higher yields are expectable. The reaction time is usually about 1 to about 20 hours.

From the reaction mixture, the keto ester compound (5) is obtained by a conventional aqueous work-up procedure. If necessary, the end compound (5) is purified by any conventional technique such as distillation, chromatography or recrystallization. If the crude product has a sufficient purity as a substrate for to the subsequent step, it can be used in the subsequent step without purification.

The second step involves reduction and lactonization of the keto ester compound (5) to the desired lactone compound (1).

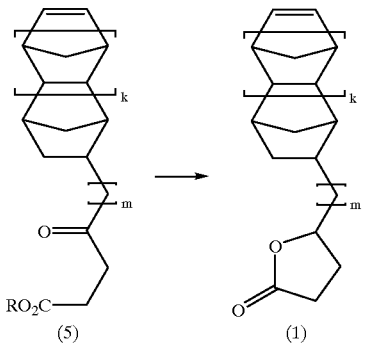

First referring to the reduction of keto group, it is important to selectively reduce only the keto group without reducing the ester group.

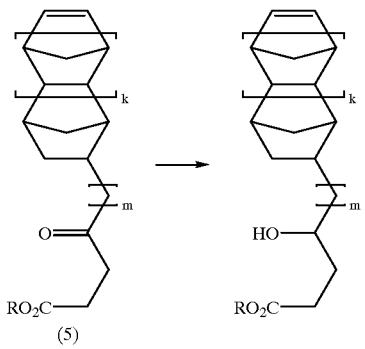

For the reduction of keto group, various reducing agents may be used. Often metal hydrides are preferably used in solvents. Exemplary metal hydrides are complex hydrides and alkoxy or alkyl derivatives thereof, including sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-t-butoxyaluminum hydride, sodium bis(2-methoxyethoxy)aluminum hydride, and lithium triethylboron hydride. The reducing agent is often used in an amount of 1.0 to 8.0 mol, preferably 1.0 to 1.5 mol of hydride per mol of the keto ester compound. The solvent may be selected in accordance with reaction conditions from water and various organic solvents including ethers such as tetrahydrofuran, diethyl ether, di-n-butyl ether and 1,4-dioxane, hydrocarbons such as n-hexane, n-heptane, benzene, toluene, xylene and cumene, alcohols such as methanol, ethanol, isopropyl alcohol and tert-butyl alcohol, and aprotic polar solvents such as dimethyl sulfoxide and N,N-dimethylformamide, alone or in admixture of any.

Reaction temperature and time vary over a wide range depending on the particular starting materials used. For example, when reduction is effected with lithium aluminum hydride in tetrahydrofuran, preferred reaction conditions include use of lithium aluminum hydride in a stoichiometric or slightly excess amount (1.0 to 1.05 equivalent as hydride) in order to avoid further reduction, a reaction temperature in the range of −80° C. to 0° C., and a reaction time of about 0.1 to 1 hour. From the reaction mixture, the hydroxy ester compound is obtained by conventional work-up. If necessary, the product may be purified by any conventional technique such as distillation, chromatography or recrystallization. If the crude product has a sufficient purity as a substrate for the subsequent step, it can be used in the subsequent step without purification. The hydroxy ester compound thus obtained is then converted to the desired lactone compound (1).

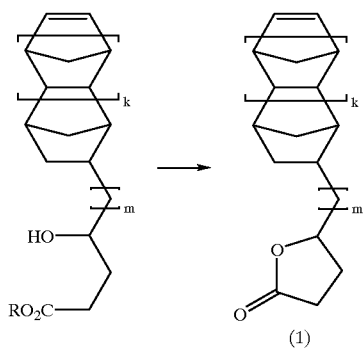

Herein, the hydroxy ester compound can be converted to the lactone compound by hydrolyzing or saponifying the ester with an aqueous alkaline solution, then neutralizing it to form a hydroxy carboxylic acid, and heating the hydroxycarboxylic acid in the presence of an acid catalyst to effect dehydrative condensation. Alternatively, the hydroxy ester compound can be converted to the lactone compound by heating it in the presence of an acid catalyst to effect alcohol-eliminating condensation. To these reactions, the same procedure as the step of converting the hydroxy diester compound (3) to the lactone compound (1) in the first method is applicable.

In the third method, the lactone compound (1) is prepared by reacting an aldehyde compound (6) with lithium 3-lithiopropionate to form a hydroxycarboxylic acid compound (7), followed by lactonization (dehydrative condensation).

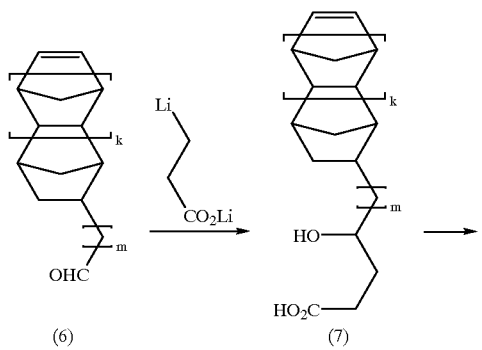

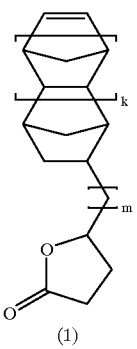

Herein k and m are as defined above.

The first step is to react an aldehyde compound (6) with lithium 3-lithiopropionate to form a hydroxycarboxylic acid compound (7).

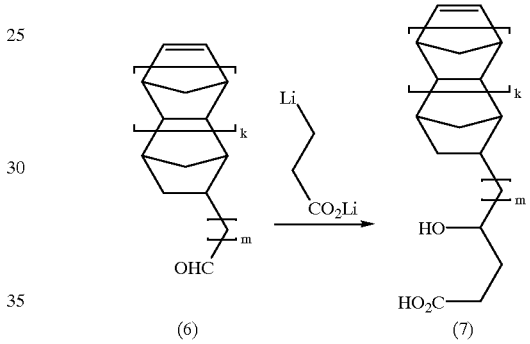

Lithium 3-lithiopropionate (dianion) is prepared by treatment of a 3-halopropionic acid with a base in a solvent. Examples of the 3-halopropionic acid are 3-bromopropionic acid and 3-iodopropionic acid. Examples of the base include lithium amides such as lithium diisopropylamide, lithium 2,2,6,6-tetramethylpiperidine, lithium bistrimethylsilylamide and lithium isopropylcyclohexylamide; alkyl lithium compounds such as trityllithium, methyllithium, phenyllithium, sec-butyllithium and tert-butyllithium; and lithium hydride. The solvent is selected in accordance with reaction conditions from ethers such as tetrahydrofuran, diethyl ether, di-n-butyl ether and 1,4-dioxane, hydrocarbons such as n-hexane, n-heptane, benzene, toluene, xylene and cumene, and polar aprotic solvents such as dimethyl sulfoxide and N,N-dimethylformamide, alone or in admixture of any. There may be used as an auxiliary a compound having a ligand such as N,N,N',N'-tetramethylethylenediamine (TMEDA), hexamethylphosphoric triamide (HMPA), N,N'-dimethylpropyleneurea (DMPU) or 1,3-dimethyl-2-imidazolidinone (DMI).

The lithium 3-lithiopropionate thus prepared is used in an amount of 0.7 to 3 mol, preferably 1.0 to 1.3 mol per mol of the aldehyde compound (6) for addition reaction to take place. Since the lithium 3-lithiopropionate is unstable at high temperature, the reaction is preferably effected under cooling, especially at a temperature of −78° C. to 0° C. The reaction time is desirably determined by monitoring the reaction until the completion by GC or silica gel TLC because higher yields are expectable. The reaction time is usually about 0.2 to about 2 hours. From the reaction mixture, the hydroxycarboxylic acid compound (7) is obtained by a conventional aqueous work-up step. If necessary, the compound (7) may be purified by any conventional technique such as distillation, chromatography or recrystallization. If the crude product has a sufficient purity as a substrate for the subsequent step, it can be used in the subsequent step without purification.

The second step involves lactonization (dehydrative condensation) of the hydroxycarboxylic acid compound (7) to the desired lactone compound (1).

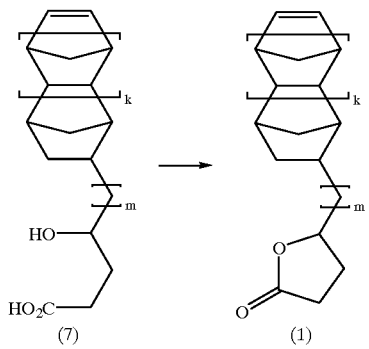

The hydroxycarboxylic acid compound can be converted to the lactone compound by heating it in the presence of an acid catalyst to effect dehydrative condensation. To this reaction, the same procedure as the step of converting the hydroxy dicarboxylic acid compound to the lactone compound (1) in the first method is applicable.

A polymer is prepared using the inventive lactone compound as a monomer. The method is generally by mixing the monomer with a solvent, adding a catalyst or polymerization initiator, and effecting polymerization reaction while heating or cooling the system if necessary. This polymerization reaction can be effected in a conventional way. Exemplary polymerization processes are ring-opening metathesis polymerization, addition polymerization, and alternating copolymerization with maleic anhydride or maleimide. It is also possible to copolymerize the lactone compound with another norbornene monomer.

A resist composition is formulated using as a base resin the polymer resulting from polymerization of the lactone compound. Usually, the resist composition is formulated by adding an organic solvent and a photoacid generator to the polymer and if necessary, further adding a crosslinker, a basic compound, a dissolution inhibitor and other additives. Preparation of the resist composition can be effected in a conventional way.

The resist composition formulated using the polymer resulting from polymerization of the inventive lactone compound lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser and firm adhesion to the substrate, a finely defined pattern having sidewalls perpendicular to the substrate can easily be formed. The resist composition is thus suitable as micropatterning material for VLSI fabrication.

EXAMPLE

Synthesis Examples and Reference Examples are given below for further illustrating the invention. It is not construed that the invention be limited to these examples.

Synthesis Examples are first described. Lactone compounds within the scope of the invention were synthesized in accordance with the following formulation.

Synthesis Example 1

Synthesis of γ-(5-norbornen-2-yl)methyl-γ-butyrolactone (Monomer 1)

In a nitrogen atmosphere, a solution in 300 g dry tetrahydrofuran of a Grignard reagent prepared from 50.0 g of 5-bromomethyl-2-norbornene by a conventional technique was added to a mixture of 47.2 g of 3-methoxycarbonyl-propionyl chloride, 4.61 g of iron (III) acetylacetonate, and 300 ml of dry tetrahydrofuran at 10° C., which was stirred for 2 hours. Then 100 g of 10% hydrochloric acid was added to stop the reaction, whereupon hexane was added for extraction. The organic layer was washed with water and aqueous saturated sodium bicarbonate solution, and concentrated in vacuum, obtaining a keto ester. The keto ester was dissolved in 100 g of tetrahydrofuran, to which 80 g of water, 5.06 g of sodium boron hydride and 10 g of methanol were successively added. The mixture was stirred for 12 hours at 20° C. for effecting reduction to a hydroxy ester. Then 50 g of 20% hydrochloric acid was added to the reaction mixture, which was stirred for one hour for lactonization. This was followed by hexane extraction, washing with water, washing with aqueous saturated sodium bicarbonate solution, and vacuum concentration. Purification by silica gel column chromatography yielded 42.1 g (yield 82%) of γ-(5-norbornen-2-yl)methyl-γ-butyrolactone.

IR (thin film): ν=3057, 2962, 2939, 2866, 1774, 1336, 1217, 1180, 1020, 978, 912 cm$^{-1}$ $^1$H-NMR of major endo-isomer (270 MHz in CDCl$_3$): δ=0.54 (1H, m), 1.15–1.45 (3H, m), 1.45–1.95 (3H, m), 2.15–2.40 (2H, m), 2.40–2.60 (2H, m), 2.70–2.85 (2H, m), 4.46 (1H, m), 5.90 (1H, m), 6.13 (1H, m).

Synthesis Example 2

Synthesis of γ-(5-norbornen-2-yl)methyl-γ-butyrolactone (Monomer 1)

In 80 g of dry tetrahydrofuran was dissolved 10.0 g of 3-bromopropionic acid. In a nitrogen atmosphere, 85.0 g of a hexane solution of 1.6M n-butyllithium was added to the solution at −78° C., followed by 30 minutes of stirring. Then a solution of 8.92 g 2-(5-norbornen-2-yl)acetaldehyde in 20 g hexamethylphosphoric triamide was added dropwise to the solution at the same temperature. With stirring, the temperature of the solution was gradually raised to 20° C. over 2 hours. Next, 80 g of 5% hydrochloric acid was added to the solution, which was stirred for one hour for lactonization. The organic layer was separated, washed with aqueous saturated sodium bicarbonate solution, washed with water, and concentrated in vacuum. Purification by silica gel column chromatography yielded 8.17 g (yield 65%) of γ-(5-norbornen-2-yl)methyl-γ-butyrolactone. The analytical properties of this compound were substantially identical with the data of Synthesis Example 1.

Synthesis Example 3

Synthesis of γ-2-(5-norbornen-2-yl)ethyl-γ-butyrolactone (Monomer 2)

In a nitrogen atmosphere, 1.84 g of metallic sodium was dissolved in 100 g of dry ethanol. Then 13.0 g of diethyl malonate was added to the solution, which was heated under reflux for one hour, forming the sodium salt of diethyl malonate. Then 11.2 g of 1,2-epoxy-4-(5-norbornen-2-yl)butane was added to the solution, which was heated under reflux for 4 hours, forming a hydroxy diester compound. Then 130 g of a 5% aqueous sodium hydroxide solution was added to the solution, which was heated under reflux for 4 hours to effect hydrolysis. The ethanol was distilled off, and 100 g of toluene and 60 g of 20% hydrochloric acid were added to the residue, which was stirred for one hour for lactonization, forming a lactone carboxylic acid. The organic layer was separated and concentrated in vacuum. Decarboxylation reaction was effected at 140° C. and 8,000 Pa. Subsequent vacuum distillation yielded 12.6 g of γ-2-(5-norbornen-2-yl)ethyl-γ-butyrolactone (boiling point: 122–127° C./67 Pa, yield: 89%).

IR (thin film): ν=3055, 2960, 2937, 2864, 1776, 1456, 1352, 1219, 1180, 1018, 982, 912 cm$^{-1}$ $^1$H-NMR of major endo-isomer (270 MHz in CDCl$_3$): δ0.49 (1H, m), 1.00–1.90 (8H, m), 1.97 (1H, m), 2.28 (1H, m), 2.45–2.55 (2H, m), 2.70–2.80 (2H, m), 4.42 (1H, m), 5.89 (1H, m), 6.11 (1H, m).

Synthesis Example 4

Synthesis of γ-2-(5-norbornen-2-yl)ethyl-γ-butyrolactone (Monomer 2)

In a nitrogen atmosphere, 11.2 g of potassium t-butoxide was dissolved in 250 g of dry tetrahydrofuran. Then 21.0 g of di-t-butyl malonate and 8.0 g of 1,2-epoxy-4-(5-norbornen-2-yl)butane were successively added to the solution, which was heated under reflux for 10 hours. The reaction solution was neutralized with 100 g of a 10% aqueous acetic acid solution, and extracted with ethyl acetate, whereupon the extracted solution was washed with water and concentrated in vacuum, obtaining a hydroxy diester compound. The hydroxy diester compound was dissolved in 200 g of toluene, which was combined with 1.0 g of p-toluenesulfonic acid and heated under reflux for 10 hours for effecting ester decomposition, lactonization and decarboxylation reaction. The reaction mixture was washed with water and concentrated in vacuum. Purification by vacuum distillation yielded 6.00 g (yield 60%) of γ-2-(5-norbornen-2-yl)ethyl-γ-butyrolactone. The analytical properties of this compound were substantially identical with the data of Synthesis Example 3.

Synthesis Example 5

Synthesis of γ-{5-(5-norbornen-2-yl)-1-pentyl}-γ-butyrolactone (Monomer 3)

In a nitrogen atmosphere, a solution in 300 g dry tetrahydrofuran of a Grignard reagent prepared from 91.8 g of 5-(5-chloro-1-pentyl)-2-norbornene by a conventional technique was added to a suspension of 69.3 g zinc chloride in 200 g dry tetrahydrofuran, forming an organozinc reagent. In the nitrogen atmosphere, the organozinc reagent was added to a mixture of 83.5 g of 3-methoxycarbonylpropionyl chloride, 5.0 g of tetrakis(triphenylphosphine)palladium(0), and 200 g of dry tetrahydrofuran at 20° C., which was stirred for 4 hours. Then 500 g of 10% aqueous ammonium chloride solution was added to stop the reaction, followed by hexane extraction, water washing and vacuum concentration, obtaining a keto ester compound. The keto ester compound was subjected to reduction, lactonization and purification as in Synthesis Example 1, yielding 97.5 g (yield 85%) of γ-{5-(5-norbornen-2-yl)-1-pentyl}-γ-butyrolactone.

IR (thin film): δ=3057, 2933, 2860, 1778, 1460, 1346, 1219, 1180, 1124, 1018, 978, 914 cm$^{-1}$ $^1$H-NMR of major endo-isomer (300 MHz in CDCl$_3$): δ=0.46 (1H, m), 0.95-2.00 (15H, m), 2.30 (1H, m), 2.40-2.60 (2H, m), 2.65-2.80 (2H, m), 4.46 (1H, m), 5.88 (1H, m), 6.08 (1H, m).

The structural formulas of Monomers 1 to 3 are shown below.

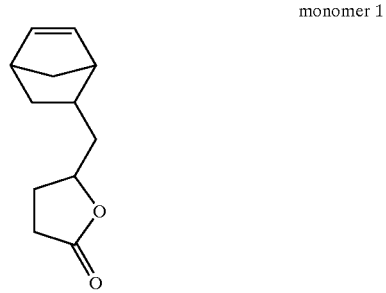

monomer 1

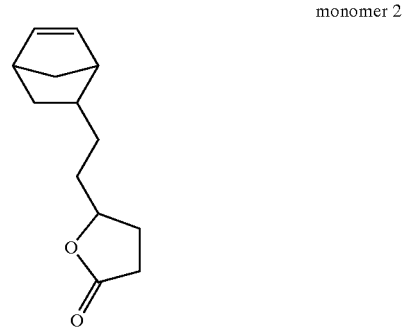

monomer 2

-continued monomer 3

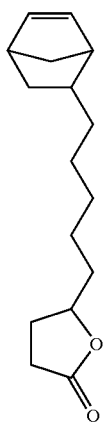

Reference Example

Polymers were synthesized using the lactone compounds obtained in the above Synthesis Examples. Using the polymers as a base resin, resist compositions were formulated, which were examined for substrate adhesion.

Polymerization reaction of tert-butyl 5-norbornene-2-carboxylate, Monomer 1, and maleic anhydride was effected using an initiator V65 (Wako Junyaku K.K.), yielding an alternating copolymer of tert-butyl 5-norbornene-2-carboxylate/γ-(5-norbornen-2-yl)methyl-γ-butyrolactone/maleic anhydride (copolymerization ratio 4/1/5).

A resist composition was prepared by blending 80 parts by weight of the above copolymer as a base resin, 1.0 part by weight of triphenylsulfonium trifluoromethanesulfonate as a photoacid generator, 480 parts by weight of propylene glycol monomethyl ether acetate as a solvent, and 0.08 part by weight of tributylamine. The composition was spin coated on a silicon wafer having hexamethyldisilazane sprayed thereon at 90° C. for 40 seconds and heat treated at 110° C. for 90 seconds, forming a resist film of 500 nm thick. The resist film was exposed to KrF excimer laser light, heat treated at 110° C. for 90 seconds, and developed by immersing in a 2.38% tetramethylammonium hydroxide aqueous solution for 60 seconds, thereby forming a 1:1 line-and-space pattern. The wafer as developed was observed under SEM, finding that the pattern down to 0.26 μm size was left unstripped.

Comparative Reference Example

For comparison purposes, a resist composition was prepared as above, using an alternating copolymer of tert-butyl 5-norbornene-2-carboxylate/maleic anhydride (copolymerization ratio 1/1). It was similarly processed, and examined for substrate adhesion. No patterns with a size of 0.50 μm or less were left.

It was confirmed that polymers resulting from the inventive lactone compounds have significantly improved substrate adhesion as compared with prior art polymers.

Japanese Patent Application No. 2000-205217 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A lactone compound of the following general formula (1):

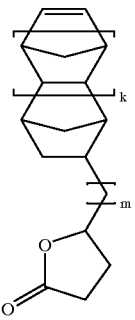

wherein k is 0 or 1 and m is an integer of 1 to 8.

2. A method for preparing a lactone compound of the following general formula (1), comprising the steps of reacting an oxirane compound of the following general formula (2) with a metallomalonate to form a hydroxy diester compound of the following general formula (3), followed by hydrolysis, decarboxylation and lactonization:

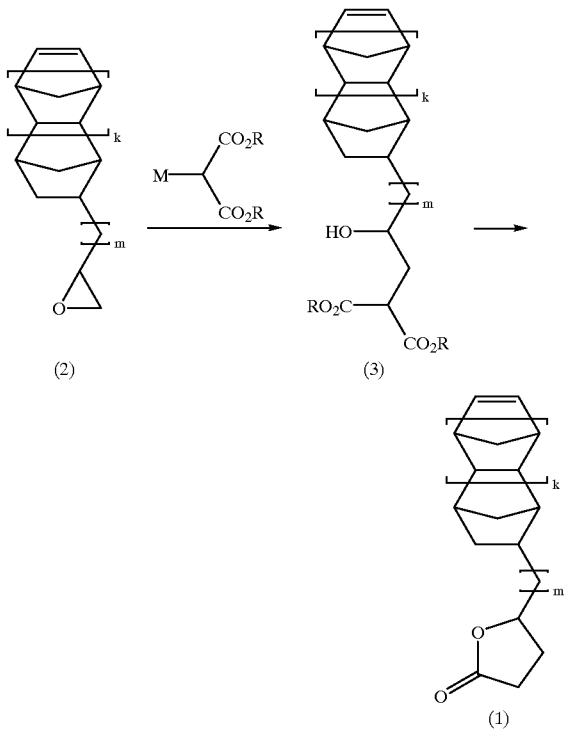

wherein k is 0 or 1, m is an integer of 1 to 8, R is alkyl, M is Li, Na, K, MgY or ZnY, and Y is halogen.

3. A method for preparing a lactone compound of the following general formula (1), comprising the steps of reacting an organometallic compound of the following general formula (4) with a 3-alkoxycarbonylpropionyl chloride to form a keto ester compound of the following general formula (5), followed by reduction and lactonization:

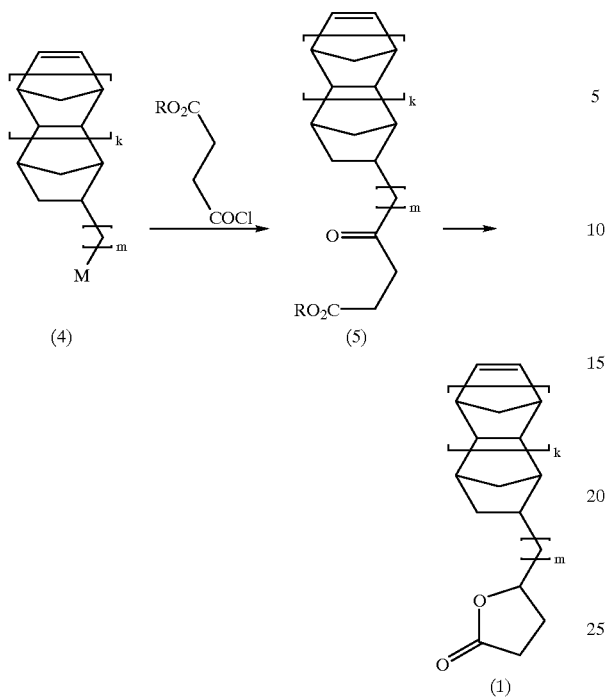

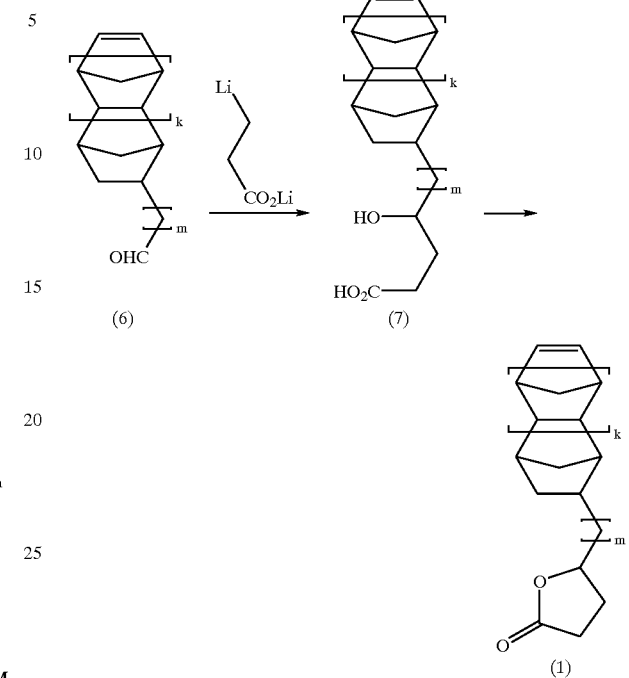

wherein k is 0 or 1, m is an integer of 1 to 8, R is alkyl, M is Li, Na, K, MgY or ZnY, and Y is halogen.

4. A method for preparing a lactone compound of the following general formula (1), comprising the steps of reacting an aldehyde compound of the following general formula (6) with lithium 3-lithiopropionate to form a hydroxycarboxylic acid compound of the following general formula (7), followed by lactonization:

wherein k is 0 or 1 and m is an integer of 1 to 8.

* * * * *